US00PP15999P2

(12) United States Plant Patent
Cain et al.

(10) Patent No.: US PP15,999 P2
(45) Date of Patent: Sep. 27, 2005

(54) APRICOT TREE NAMED 'SUAPRITEN'

(50) Latin Name: *Prunus armeniaca*
Varietal Denomination: Suapriten

(75) Inventors: David W. Cain, Bakersfield, CA (US); Terry A. Bacon, Bakersfield, CA (US); Bruce D. Mowrey, Watsonville, CA (US)

(73) Assignee: Sun World International, Inc., Bakersfield, CA (US)

( * ) Notice: Subject to any disclaimer, the term of this patent is extended or adjusted under 35 U.S.C. 154(b) by 43 days.

(21) Appl. No.: 10/871,270

(22) Filed: Jun. 17, 2004

(51) Int. Cl.[7] ..... A01H 5/00
(52) U.S. Cl. ..... Plt./186
(58) Field of Search ..... Plt./186

(56) References Cited

U.S. PATENT DOCUMENTS

PP9,593 P 6/1996 Zaiger et al. ..... Plt./186

*Primary Examiner*—Anne Marie Grunberg
*Assistant Examiner*—June Hwu
(74) *Attorney, Agent, or Firm*—Knobbe, Martens, Olson & Bear, LLP

(57) ABSTRACT

A new and distinct apricot, *Prunus armeniaca* cv. 'Suapriten' that ripens early in the season and produces heavy, consistent crops in early districts of the California San Joaquin Valley. Harvest begins about five days after the apricot variety 'Poppy' (U.S. Plant Pat. No. 9,593) harvest begins. The fruit is large (averaging approximately 61 mm), firm and develops a bright golden-orange color with red blush on exposed fruit. The flavor has been judged to be superior to other early-season apricots with approximately 15° brix that is well balanced by a slightly tart skin, a slight aroma, and plentiful juice.

1 Drawing Sheet

Latin name of the genus and species claimed: *Prunus armeniaca.*
Variety denomination: 'Suapriten'.

BACKGROUND OF THE INVENTION

The present invention relates to a new and distinct variety of apricot tree, herein after referred to by the cultivar name 'Suapriten.' The new variety 'Suapriten' originated by hybridization, and was first hybridized by Bruce Mowrey. The new variety was selected by David Cain and was evaluated by David Cain and Terry Bacon near Wasco, Calif. in Kern County.

SUMMARY OF THE INVENTION

The new variety is characterized by having firm, large fruit (averaging approximately 61 mm in diameter) that develops a bright golden-orange color with red blush on sunlight-exposed fruit. The flavor is superior to other early-season apricots, with approximately 15° brix that is well balanced by a slightly tart skin, a slight aroma, and plentiful juice. The new variety 'Suapriten' ripens early in the season and produces heavy, consistent crops in early districts of the California San Joaquin Valley relative to other early apricot varieties. Harvesting of 'Suapriten' typically begins in the second week of May in Kern County, Calif., approximately seven days after the beginning of harvesting of the apricot variety 'Poppy' (U.S. Plant Pat. No. 9,593).

The seed parent of the new variety 'Suapriten' is '063-160' (unpatented) and the pollen parent is '90A-006' (unpatented). The parent varieties were first crossed in 1992, with the date of planting of February 1993, and the time of first flowering being February of 1995. The new apricot variety was first asexually propagated by David Cain near Wasco, Kern County, Calif. in 1997 by budding onto 'Nemaguard' (unpatented) rootstock.

The new variety 'Suapriten' can be distinguished from its seed parent, '063-160' in that the fruit ripens approximately five days earlier, and is larger and firmer than the fruit of the seed parent. The new variety can be distinguished from its pollen parent, '90A-006' in that the fruit is larger and develops red blush in sunlight while the fruit of the pollen parent '90A-006' does not.

The new apricot variety 'Suapriten' may be distinguished from presently available cultivars in commerce by the following combination of characteristics: The new variety most nearly resembles the apricot variety 'Poppy' (U.S. Plant Pat. No. 9,593). It may be distinguished from 'Poppy' by ripening approximately seven days later, having larger sized fruits (averaging approximately 61 mm in diameter compared with approximately 58 mm in diameter with 'Poppy'), and having more red blush on exposed fruit.

The new variety 'Suapriten' has been shown to maintain its distinguishing characteristics through successive asexual propagations by, for example, budding onto 'Nemaguard' rootstock.

BRIEF DESCRIPTION OF THE FIGURE

The accompanying color photographic illustration (FIG. 1) shows typical specimens of the foliage and fruit of the new apricot variety 'Suapriten.' The illustration shows the upper and lower surface of the leaves, an exterior and sectional view of a fruit divided across its suture plane to show flesh color, pit cavity and stone remaining in place.

The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The new variety 'Suapriten' has not been observed under all possible environmental conditions. The phenotype may vary somewhat with variations in environment such as temperature, daylength, and light intensity, without, however, any variance in genotype.

The descriptive matter which follows pertains to eight year old 'Suapriten' plants grown in the vicinity of Wasco, Kern County, Calif., during 2002 and is believed to apply to plants of the variety grown under similar conditions of soil and climate elsewhere.

TREE

General: (measurements taken on 8 year old tree unless otherwise noted).

*Tree size.*—Large. Normal for most apricot varieties. Reaches a height of approximately 3.5 meters including normal pruning.

*Tree vigor.*—Vigorous. Growth of approximately 1.8 to approximately 2 meters height the first growing season.

*Tree growth.*—Upright-spreading.

*Tree productivity.*—Productive. Fruit set is usually two or more times the desired amount for marketable size fruit. Thinning and spacing of fruit is necessary.

*Tree form.*—Vase formed.

*Bearer.*—Regular. No alternate bearing observed.

*Fertility.*—Partially self-fertile. Suapriten has set well under tent to exclude bees, but pollinator variety may increase set.

*Tree canopy density.*—Dense. Pruning is required to open tree vase shape, allowing more sunlight to center of tree.

*Tree hardiness.*—Hardy in all fruit growing areas of California. Winter chilling requirement is approximately 500 hours at or below 7.2° C.

*Tree disease resistance/susceptibility.*—No specific testing for relative plant disease resistance/susceptibility has been designed. Under close observation in area described in Wasco, Kern County, Calif., no particular plant/fruit disease resistance/susceptibility has been observed.

Trunk: (measurements at 30 cm above soil line).

*Trunk diameter.*—Approximately 19 cm. Varies with soil type, fertility, climatic conditions and cultural practices.

*Trunk texture.*—Smooth to slightly shaggy; increases with age of tree.

*Trunk color.*—Near Greyed-green 197D in exposed areas to near Greyed-orange 166A in recesses, becoming darker with age.

Branches: (measurements at approximately 90 cm above soil line).

*Branch diameter.*—Approximately 8 to approximately 9 cm.

*Branch texture.*—Smooth on 1$^{st}$ year wood, increasing roughness with tree age.

*Branch color.*—Branches vary from near Greyed-green 197D to near Greyed-green 197B in exposed areas and near Greyed-orange 165B in recesses.

*Branch lenticels.*—Number:Few — varies from 0 to approximately 3 per square centimeter. Lenticel number varies widely depending on environmental conditions and vigor of the plant. Color: Near Greyed-white 156A. Typical size: Approximately 4 mm in length and approximately 2 mm wide.

Flowering shoots: (data taken in July at midpoint of current-season growth).

*Flowering shoot size.*—Average diameter; approximately 5 mm.

*Flowering shoot color.*—Topside: Near Greyed-orange 165A. Underside: Near Greyed-orange 165A.

*Flowering shoot lenticels.*—Few — varies from approximately 2 to approximately 7 per linear centimeter. Lenticel number varies widely depending on environmental conditions and vigor of the plant.

*Flowering shoot leaf buds.*—Shape: Ovoid. Width: Approximately 1.5 mm. Length: Approximately 2 mm. Color: Near Greyed-orange 165A.

*Flowering shoot flower buds.*—Shape: Elongated ovoid. Width: Approximately 1.5 mm. Length: Approximately 4 mm. Color: Approximately Near Greyed-orange 165A. Number: Usually 2.

LEAVES (data taken in July on fully expanded leaf at midpoint of current-season growth)

*Leaf size.*—Average length: Approximately 75 mm. Average width: Approximately 70 mm.

*Leaf thickness.*—Medium.

*Leaf color.*—Upper surface: Approximately Green 136B. Lower surface: Approximately Green 139B.

*Leaf form.*—Circular.

*Leaf tip.*—Cuspidate.

*Leaf base.*—Rounded-to-truncate.

*Leaf margin.*—Slightly serrated.

*Venation.*—Pinately net veined.

*Leaf surface texture.*—Smooth.

*Leaf petiole.*—Average length: Approximately 34 mm. Average diameter: Approximately 1.5 mm. Color: Near Red 53B.

*Leaf glands.*—Form: Globose. Number: Varies from 0 to approximately 5. Position: Alternate on upper portion of petiole and base of leaf blade. Average size: Approximately 0.7 mm by approximately 0.7 mm. Color: Near Greyed-orange 165A.

FLOWERS (fully opened)

General:

*Flower blooming period.*—First bloom: Feb. 19, 2002. Full bloom: Feb. 24, 2002.

*Flower size.*—Average diameter: approximately 28 mm.

*Flower aroma.*—Very slight.

Flower peduncle:

*Length.*—Approximately 3 mm.

*Diameter.*—Approximately 2 mm.

*Color.*—Near Yellow-green 145C, with highlights of near Red 46D.

Flower petals:

*Number.*—5.

*Arrangement.*—Overlapping.

*Length.*—Approximately 13 mm.

*Diameter.*—Approximately 11 mm.

*Shape.*—Circular.

*Apex shape.*—Rounded.

*Base shape.*—Narrows at point of attachment.

*Color.*—White.

*Surface texture.*—Smooth.

*Margins.*—Smooth.

Flower sepals:
*Number.*—5.
*Length.*—Approximately 6 mm.
*Diameter.*—Approximately 4.5 mm.
*Shape.*—Elliptical with cuspidate apex.
*Color.*—Near Red 47A.
*Surface texture.*—Smooth.

Flower stamens:
*Number.*—Approximately 14 to 18, average approximately 17.
*Average length.*—Approximately 10 mm.
*Filament color.*—White.
*Anther color.*—Near Yellow 12B.
*Pollen color.*—Near Yellow 12B.

Flower pistil:
*Number.*—Usually one, occasionally two.
*Average length.*—Approximately 8 mm.
*Ovary diameter.*—Approximately 3 mm.
*Pubescence.*—Heavy.
*Stigma position.*—Level with anthers.

FRUIT (data taken at firm-ripe on mature tree managed to obtain maximum quality)

General:
*Fruit harvest.*—Date of first pick: Approximately May 14, 2002. Date of last pick: Approximately May 24, 2002.

Fruit size:
*Length* (*stem end to apex*).—Approximately 60 mm.
*Diameter in line with suture plane.*—Approximately 61 mm.
*Diameter perpendicular to suture plane.*—Approximately 61 mm.
*Average weight.*—Approximately 110 gm.

Fruit form:
*Viewed from apex.*—Rounded with slightly pronounced suture. Viewed from side, facing suture: Oblong, slightly asymmetrical. Viewed from side, perpendicular to suture: Oblong, asymmetrical.

Fruit apex shape: Rounded, indented, asymmetrical, one half longer than the other.

Fruit stem-end cavity depth: Shallow.

Fruit stem:
*Length.*—Approximately 8 mm.
*Diameter.*—Approximately 2 mm.
*Color.*—Near Green 143C.

Fruit skin:
*Thickness.*—Medium.
*Adherence to flesh.*—Tenacious.
*Surface texture.*—Smooth.
*Pubescence.*—Short, with moderate amount.
*Ground color.*—Orange, near Yellow-orange 20B.
*Overcolor.*—Some red blush, near Orange-red 34A developing where fruit is exposed to sunlight.
*Taste.*—Mildly acidic.

Fruit flesh:
*Ripens.*—Evenly.
*Texture.*—Fine, firm.
*Fibers.*—Few, short.
*Flavor.*—Sweet-tart.
*Brix.*—Approximately 15°.
*Juice.*—Moderate.
*Aroma.*—Slight.
*Color.*—Orange, near Orange 26A to near Orange 24A.
*Pit cavity color.*—Near Orange 26A.
*Pit cavity length.*—Approximately 35 mm.
*Pit cavity diameter in line with suture plane.*—Approximately 25 mm.
*Pit cavity diameter perpendicular to suture plane.*—Approximately 14 mm.

Fruit use: Dessert. Market, local and long distance.

Fruit shipping/keeping quality: Good. Holds well in cold storage for three weeks and maintains good firmness and eating quality. Minimal bruising and scarring in packing and shipping trials.

Stone: (measurements taken on dried stones)
*Stone freeness.*—Semi-freestone.
*Stone size.*—Length: Approximately 35 mm. Diameter in line with suture plane: Approximately 25 mm. Diameter perpendicular to suture plane: Approximately 14 mm.
*Stone form* (*viewed from side*).—Oblong.
*Stone form* (*viewed from stem end*).—Oval, flattened.
*Stone base shape.*—Rounded, retuse at stem attachment.
*Stone apex shape.*—Rounded with a slight dull point.
*Stone surface.*—Irregularly furrowed near base. Heavily ridged throughout. Lightly pitted throughout.
*Stone halves.*—Equal.
*Stone ridges.*—One well-developed ridge is present on each side of the suture. The ridge is narrow, beginning at the base and extending throughout the length of the stone.
*Stone outgrowing keel.*—Well developed.
*Stone tendency to split.*—None.
*Stone color.*—Near Greyed-orange 164C.

What is claimed is:

1. A new and distinct variety of apricot tree named 'Suapriten' as herein illustrated and described.

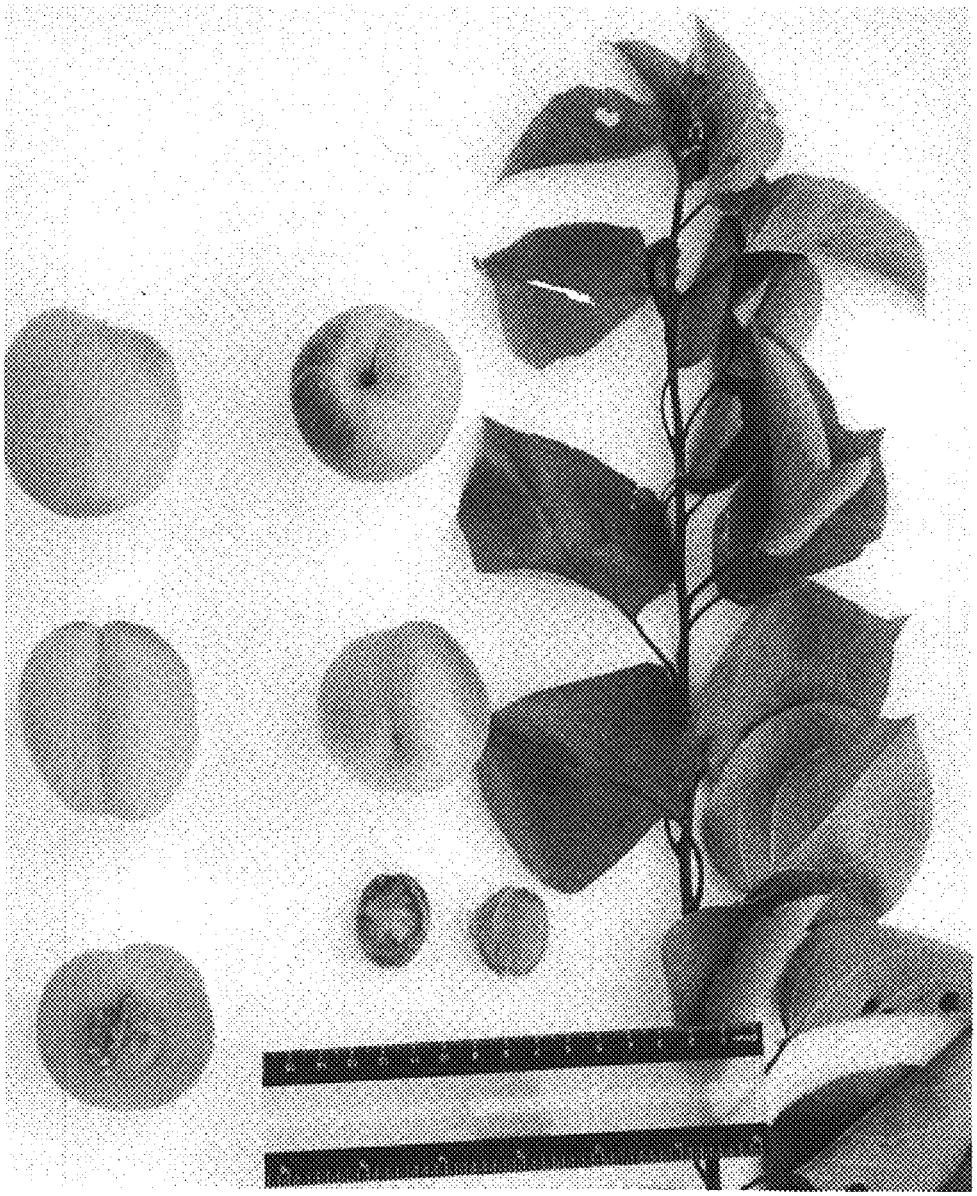

* * * * *